US005529922A

United States Patent [19]
Chapman et al.

[11] Patent Number: 5,529,922
[45] Date of Patent: Jun. 25, 1996

[54] ANTI-IDIOTYPIC MONOCLONAL ANTIBODY THAT INDUCES AN IMMUNE RESPONSE AGAINST THE GANGLIOSIDE $GD_3$ AND HYBRIDOMA PRODUCING SAID ANTIBODY

[75] Inventors: Paul B. Chapman; Alan N. Houghton, both of New York, N.Y.

[73] Assignee: Sloan-Kettering Institute for Cancer Research, New York, N.Y.

[21] Appl. No.: 445,906

[22] Filed: May 22, 1995

Related U.S. Application Data

[63] Continuation of Ser. No. 111,262, Aug. 24, 1993, abandoned, which is a continuation of Ser. No. 357,037, May 25, 1989, abandoned.

[51] Int. Cl.[6] .............................. C12N 5/20; C07K 16/42
[52] U.S. Cl. .................. 435/240.27; 530/387.2; 530/387.3; 530/387.5; 530/388.8
[58] Field of Search ........................ 435/240.27, 172.1, 435/70.21, 7.23; 530/387.2, 387.3, 387.5, 388.8

[56] References Cited

U.S. PATENT DOCUMENTS 4,918,164  4/1990  Hellstrom et al. .

OTHER PUBLICATIONS

Tadashi Tai, et al. (1985) *Int. J. Cancer*, 35;607–612.
Livingston, P. O. et al. (1985), *Cancer* 55:713–720.
Saroj Vadhan–Raj et al. (1988) *Journal of Clinical Oncology*, vol. 6, No. 10 1636–1648 (Exhibit D).
John R. Schreiber, et al. (1988) *Clinical Research*, vol. 36, No. 3 (Exhibit E).
Giovanna Viale, et al. (1989) *The Journal of Immunology*, 143:4338–4344 (Exhibit A).
Kathryn E. Stein, et al. (1984) *Journal of Experimental Medicine* 160:1001–1011 (Exhibit C).
Dippold et al. (1980) Proc. Nat'l Acad. Sci., U.S.A. 77(10): 6114–6118 (Exhibit 2).
Nepom et al. (1987) Cancer and Metastasis Reviews, 6, :489–502 (Exhibit 3).
Morrison et al. (1985) Science, 229:1202–1207 (Exhibit 4).
Hellstrom, PNAS, 82, 1499–1502 (1985).
Houghton et al, PNAS 82, 1242–1246 (1985).
Cherek et al, PNAS, 82: 5155–9 (1985).
Hastings et al. *Cancer Res.* 52:1681–1686, 1992.
Anderson et al. J. Immunotherapy 11:267–273, 1992.
Davis et al., Nature 358:76–79, 1992.
Bentley et al., Nature 348:254–257, 1990.
Shin et al. Mtds in Enzymology 178:459–476, 1989.
Oi et al., Biotechniques 4:214–221, 1986.
Morrison et al. Clinical Chemistry 34: 1668–1675, 1988.
Hodgson, Biotechnology 9:421–424 1991.
Hird et al. in "Genes and Cancer", Carney et al. Eds John Wiley & Sons 1990, pp. 183–189.
Young et al., J. Exp. Med. 150: 1008, 1979.
Kerlin et al., Research in Veterinary Science 41: 191, 1986.
Staruch et al. J. Immunol. 130:2191, 1983.

*Primary Examiner*—Paula K. Hutzell
*Attorney, Agent, or Firm*—John P. White

[57] ABSTRACT

The invention provides an anti-idiotypic monoclonal antibody, IgG2b subclass, which specifically induces an immune response against the $GD_3$ ganglioside and specifically binds to the binding site of the R24 antibody.

6 Claims, 11 Drawing Sheets

FIGURE 2
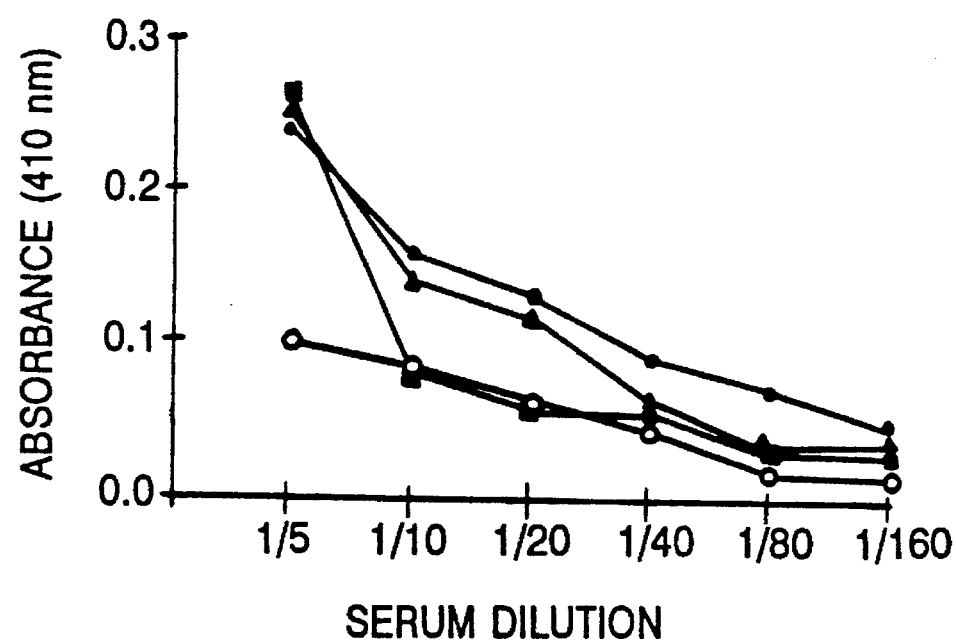

FIGURE 11
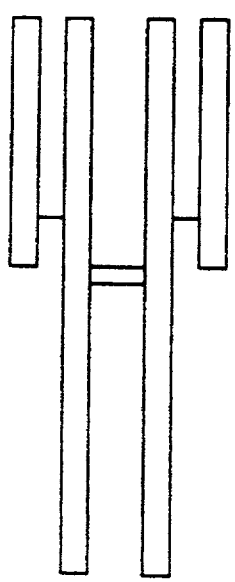 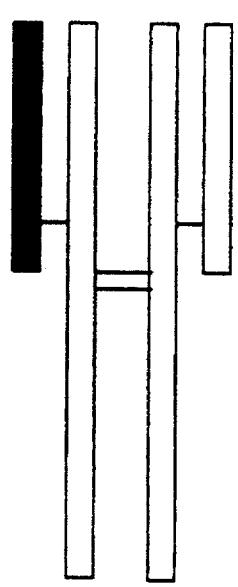 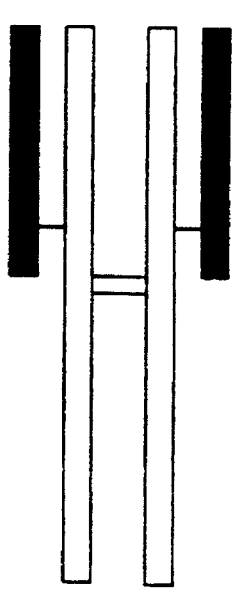
R24  V2-R24  V1-R24
Light Chain: ▢ R24
▬ NS-1

ANTI-IDIOTYPIC MONOCLONAL ANTIBODY THAT INDUCES AN IMMUNE RESPONSE AGAINST THE GANGLIOSIDE GD₃ AND HYBRIDOMA PRODUCING SAID ANTIBODY

The invention disclosed herein was made with Government support under NIH Grant No. CA 08748 from the Department of Health and Human Services. Accordingly, the U.S. Government has certain rights in this invention.

This application is a continuation of application Ser. No. 08/111,262, filed Aug. 24, 1993, now abandoned, which is a continuation of application Ser. No. 07/357,037, filed May 25, 1989, now abandoned.

BACKGROUND OF THE INVENTION

R24, an IgG3 mouse monoclonal antibody (mAb) raised against human melanoma, recognizes the ganglioside $GD_3$. $GD_3$ is abundantly expressed on most melanomas but is expressed only to a limited extent and at a low concentration on normal tissues.

R24 is a mixture of three molecular species (FIG. 11). The species have been designated V1-R24, V2-R24, and R24. In V1-R24 and V2-R24, one or both of the light chains, respectively, have been replaced by an irrelevant light chain. These molecules show very little R24-like activity. Only the third molecular species is completely intact and is the "true" R24. This implies that the $GD_3$-binding regions (also termed "paratopes") of V1-R24 and V2-R24 are altered as compared to R24. We developed a method of purifying R24 to isolate the three species. This method employs an ion-exchange chromatography column (Mono Q, Pharmacia, Inc.).

Phase 1 trial of R24 in melanoma patients resulted in 4 out of 21 objective responses. For these reasons, $GD_3$ is an appealing target for immunotherapy of cancer.

Anti-idiotypic monoclonal antibodies to R24 are expected to carry the internal image of $GD_3$. Such a monoclonal antibody is a valuable immunological reagent. $GD_3$ is poorly immunogenic; however, we find that immunization with an R24 anti-idiotypic mAb results in an anti-$GD_3$ immune response with high titer.

The present invention, BEC2, is an anti-idiotypic monoclonal antibody which was made against the anti-$GD_3$ monoclonal antibody R24.

SUMMARY OF THE INVENTION

The invention provides an anti-idiotypic monoclonal antibody, IgG2b subclass, which specifically induces an immune response against the GD3 ganglioside and specifically binds to the binding site of the R24 antibody.

BRIEF DESCRIPTION OF THE FIGURES

FIG. 2: Anti-$GD_3$ reactivity induced in rabbits by immunization with BEC2. Rabbits were inoculated subcutaneously with 100 μl of BEC2 in complete Freund's adjuvant. Subsequent booster immmunizations were administered either subcutaneously in incomplete Freund's adjuvant (Days 17 and 31) or intramuscularly without adjuvant (Days 57 and 85). To detect anti-$GD_3$ rabbit antibodies by ELISA, 96-well plates were coated with purified melanoma $GD_3$ and blocked with 5% non-fat milk. Dilutions of rabbit serum were added for 1 hour. After washing, alkaline phosphatase-conjugated anti-rabbit IgG was added. Binding was visualized by adding substrate (p-nitrophenyl-phosphate) and measuring the absorbance at 410 nm.

FIG. 11 shows variants of monoclonal antibody R-24. In variant V1-R24, both light chains are replaced by the light chain from NS-1; in variant V2-R24, only one of the light chains has been replaced by the NS-1 light chain.

DETAILED DESCRIPTION OF THE INVENTION

Figure 1:
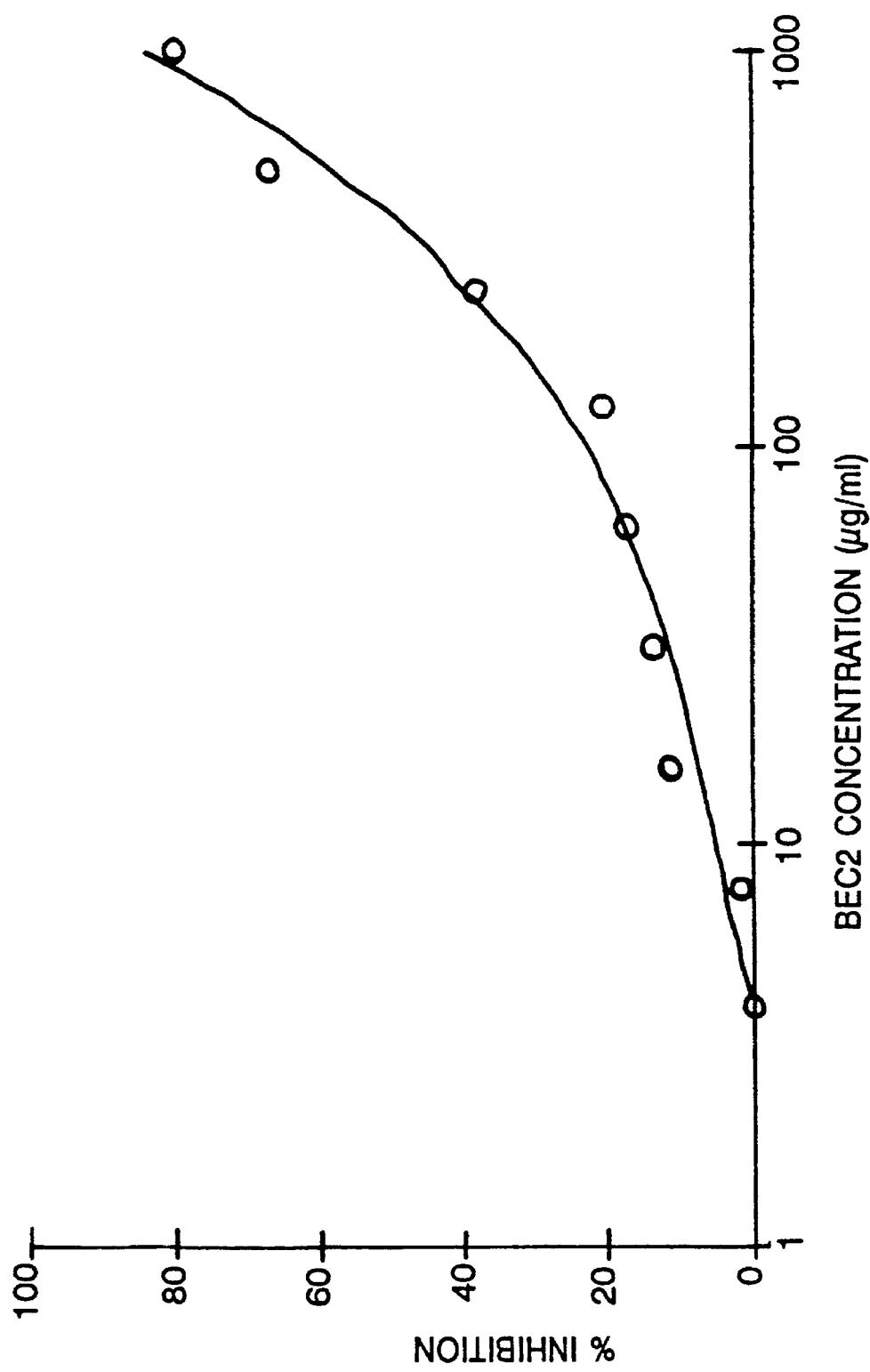
FIG. 1: Inhibition of R24 binding to $GD_3$ by BEC2. Dilutions of BEC2 were incubated with 5 μg/ml of biotinylated R24 for 1 hour. The mixture was then plated into wells coated with melanoma gangliosides containing $GD_3$. Binding of R24 was detected by adding alkaline phosphatase-conjugated avidin for 15 minutes. After washing, substrate (p-nitrophenylphosphate) was added and the absorbance at 410 nm was measured.
Figure 3:
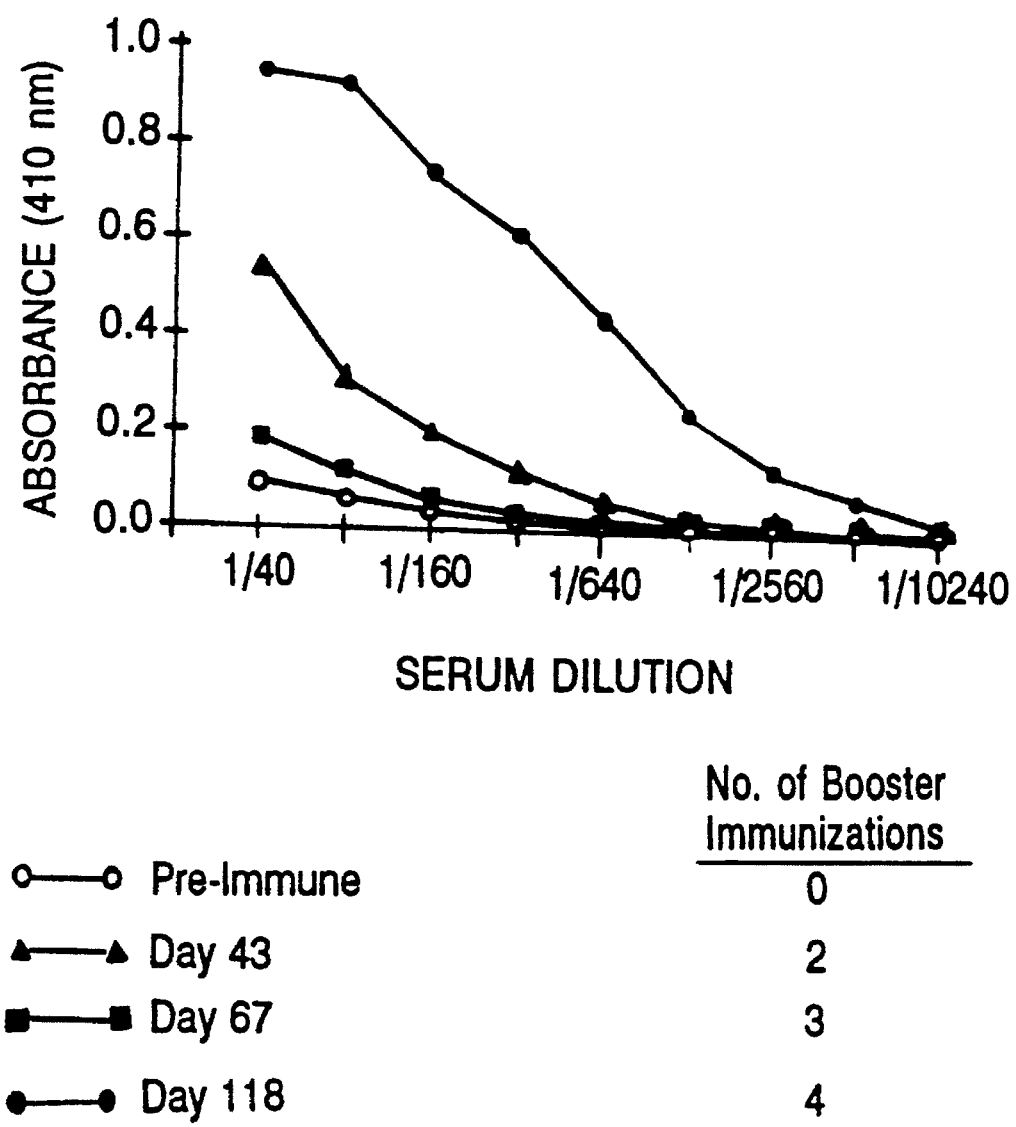
FIG. 3: Anti-$GD_3$ reactivity induced in rabbits by immunization with BEC2. Rabbits were inoculated subcutaneously with 100 μl of BEC2 in complete Freund's adjuvant. Subsequent booster immunizations were administered either subcutaneously in incomplete Freund's adjuvant (Days 17 and 31) or intramuscularly without adjuvant (Days 57 and 85). To detect anti-$GD_3$ rabbit antibodies by ELISA, 96-well plates were coated with purified melanoma $GD_3$ and blocked with 5% non-fat milk. Dilutions of rabbit serum were added for 1 hour. After washing, alkaline phosphatase-conjugated anti-rabbit IgM was added. Binding was visualized by adding substrate (p-nitrophenyl-phosphate) and measuring the absorbance at 410 nm.

The present invention provides an anti-idiotypic monoclonal antibody, e.g. a mouse anti-idiotypic monoclonal antibody or a genetically engineered to a human/mouse chimaric monoclonal antibody, which induces an immune response against the gangliosiae GD3 and specifically binds to the binding site of the R24 antibody. The anti-idiotypic antibody is designated BEC2. Further, the paratope of BEC2 mimics the GD3 ganglioside.

A hybridoma designated BEC2 hybridoma (ATCC Accession No. HB 10153) which produces the anti-idiotypic monoclonal antibody is also provided in the invention. The BEC2 hybridoma has been deposited on May 23, 1989, pursuant to the Budapest Treaty On the International Recognition Of The Deposit of Microorganisms For The Purposes of Patent Procedure with the Patent Culture Depository of the American Type Culture Collection (ATCC), 12301 Parklawn Drive, Rockville, Md. 20852 U.S.A. under ATCC Accession No. HB 10153.

In one embodiment, the anti-idiotypic monoclonal antibody, BEC2, is labeled with a detectable marker. An example of the detectable marker includes a chromophore, a fluorophore, a radioisotope, or a heavy metal. In another embodiment the detectable marker is created by an enzyme reaction, for example, avidin conjugated to alkaline-phosphatase.

Additionally, the invention provides a method of producing the BEC2 anti-idiotypic monoclonal antibody. The method comprises purifying R24 monoclonal antibodies, attaching the R24 monoclonal antibodies onto the surface of *Staphylococcus aureus* so as to produce an immunogen, combining the immunogen with interleukin 1, e.g. recombinant human interleukin 1, so as to produce a novel immunogen-adjuvant combination, and injecting the novel immunogen-adjuvant combination into syngeneic mice thereby producing the BEC2 anti-idiotypic monoclonal antibody.

Further provided in this invention is a vaccine comprising an effective immunizing amount of the anti-idiotypic monoclonal antibody, BEC2, and a pharmaceutically acceptable carrier. The vaccine may be used as part of a method of immunizing a human subject against GD3 gangliosides. The method comprises administering to the subject, e.g., by intravenous, intraperitoneal, subcutaneous, intramuscular, topical, or intradermal means, an effective immunizing amount of the vaccine.

Further, a method of treating a human subject with a neoplastic or preneoplastic condition is provided wherein the method comprises administering to the subject, e.g. by intravenous, intraperitoneal, subcutaneous, intramuscular or intradermal means, an effective amount of the BEC2 anti-idiotypic monoclonal antibody and a pharmaceutically acceptable carrier. Examples of neoplastic or preneoplastic conditions include melanomas, sarcomas, T lymphocyte malignancies, Hodgkin's disease, malignancies associated with the expression of GD3 gangliosides, lung cancers, or brain tumors.

A pharmaceutically acceptable carrier includes all carriers known in the art. Merely by may of example, the carrier may be saline.

Finally, this invention is illustrated in the Experimental Details section which follows. This section is set forth to aid in an understanding of the invention but is not intended to, and should not be construed to, limit in any way the invention as set forth in the claims which follow.

EXPERIMENTAL DETAILS

Anti-idiotypic mAbs to R24

We immunized syngeneic (C57B1/6X BALB/C)F1 female mice with purified R24 free of either variant. The significance of using syngeneic mice is that the only portion of the R24 molecule which should be recognized as foreign is the paratope. It is standard to mix the immunizing material with an "adjuvant" which boosts the immune response of the mouse. We used a novel adjuvant by sticking the R24 onto the surface of *Staphylcoccus aureus* cells and injecting the R24-coated cells along with rhIL-1 (DuPont).

The mice received two weekly boosts. Three days before fusion, mice were injected with 50 μg R24 i.v. Splenocytes were fused with SP2/0 using standard techniques. Hybridomas were screened for the ability to bind to R24 F(ab')$_2$ fragments using an alkaline phosphatase conjugated goat anti-mouse F$_c$-specific second antibody. Positive colonies were subcloned twice by limiting dilution. Both *Staph A* and IL-1 are strong stimulators of B lymphocytes. Using standard hybridoma techniques and fusion of immune mouse spleen cells to the SP2/0 mouse myeloma cell line BEC2 and BEC3 were produced.

Demonstrating that BEC2 is an Anti-idiotypic mAb
BEC2 recognizes unique determinants on R24

If BEC2 is indeed an anti-idiotype for R24, it would be expected that BEC2 would bind only to R24 and no other mAb. We have tested the ability of BEC2 to bind to 23 other mAbs using an inhibition assay. No mAb, other than R24, can compete with R24 for BEC2 binding (Table 1). It is notable that V1-R24, the variant with two irrelevant light chains, is not bound by BEC2. This is consistent with the model that BEC2 recognizes the paratope of R24.

The results in Table 1 were obtained using the following method. BEC2 (5 μg/ml) was pre-incubated with dilutions of inhibiting mAb for 1 hr. The mixture was then, plated into wells previously coated with R24 F(ab')$_2$ fragments and blocked with 5% non-fat milk. BEC2 binding was detected by ELISA using an alkaline phosphatase-conjugated second antibody specific for the F$_c$ region.

TABLE 1

Ability of BEC2 to bind to various monoclonal antibodies as measured by the ability of the monoclonal antibody to prevent binding of BEC2 to R24. Inhibition of BEC2 binding to R24 F(ab')$_2$ Fragments by a Panel of mAb.

| Antibody | Isotype | Specificity | IC$_{50}$[1] |
| --- | --- | --- | --- |
| 1. MOPC104E | M | α1 -> 3 dextrans | 390 |
| 2. TEPC183 | M | ND[2] | 425 |
| 3. MOPC315 | A | Dinitrophenol | >900 |
| 4. TEPC15 | A | Phosphoryl choline | >900 |
| 5. MOPC21 | G1 | ND | >700 |
| 6. HT29-15 | G1 | Adenocarcinoma | >900 |
| 7. 455 | G1 | EGF receptor | >900 |
| 8. M111 | G1 | gp110 | 465 |
| 9. S22 | G1 | ND | >1000 |
| 10. 2G10 | G1 | gp76 | >1000 |
| 11. C350 | G1 | gp180 | >500 |
| 12. UPC10 | G2a | β2-6 fructosan | >900 |
| 13. TA99 | G2a | gp75 | >900 |
| 14. A33 | G2a | ND | >900 |

TABLE 1-continued

Ability of BEC2 to bind to various monoclonal
antibodies as measured by the ability of the monoclonal
antibody to prevent binding of BEC2 to R24. Inhibition
of BEC2 binding to R24 F(ab')$_2$ Fragments by a Panel of
mAb.

| Antibody | Isotype | Specificity | IC$_{50}$[1] |
|---|---|---|---|
| 15. M195 | G2a | CD33 | >1000 |
| 16. F23 | G2a | CD13 | >1000 |
| 17. MOPC141 | G2b | ND | 485 |
| 18. OKB7 | G2b | CD21 | >1000 |
| 19. FLOPC21 | G3 | ND | >900 |
| 20. Y5606 | G3 | AMP/purine/tri-ethanolamine | >500 |
| 21. F36/22 | G3 | Breast Carcinoma | >1000 |
| 22. 3F8 | G3 | GD2 ganglioside | >1000 |
| 23. V1-R243 | G3 | GD3 ganglioside | 425 |
| 24. R24 | G3 | GD3 ganglioside | 26 |

[1]IC$_{50}$ is the concentration of inhibiting mAb (in μg/ml) required to inhibit 50% of BEC2 binding to R24 F(ab')$_2$ fragments.
[2]Not Determined
[3]A variant of R24 in which both light chains are replaced with MOPC 21 myeloma light chains. This results in a mAb with >40-fold lower affinity for GD$_3$.

BEC2 carries the internal image of the original
antigen GD$_3$

Figure 4:
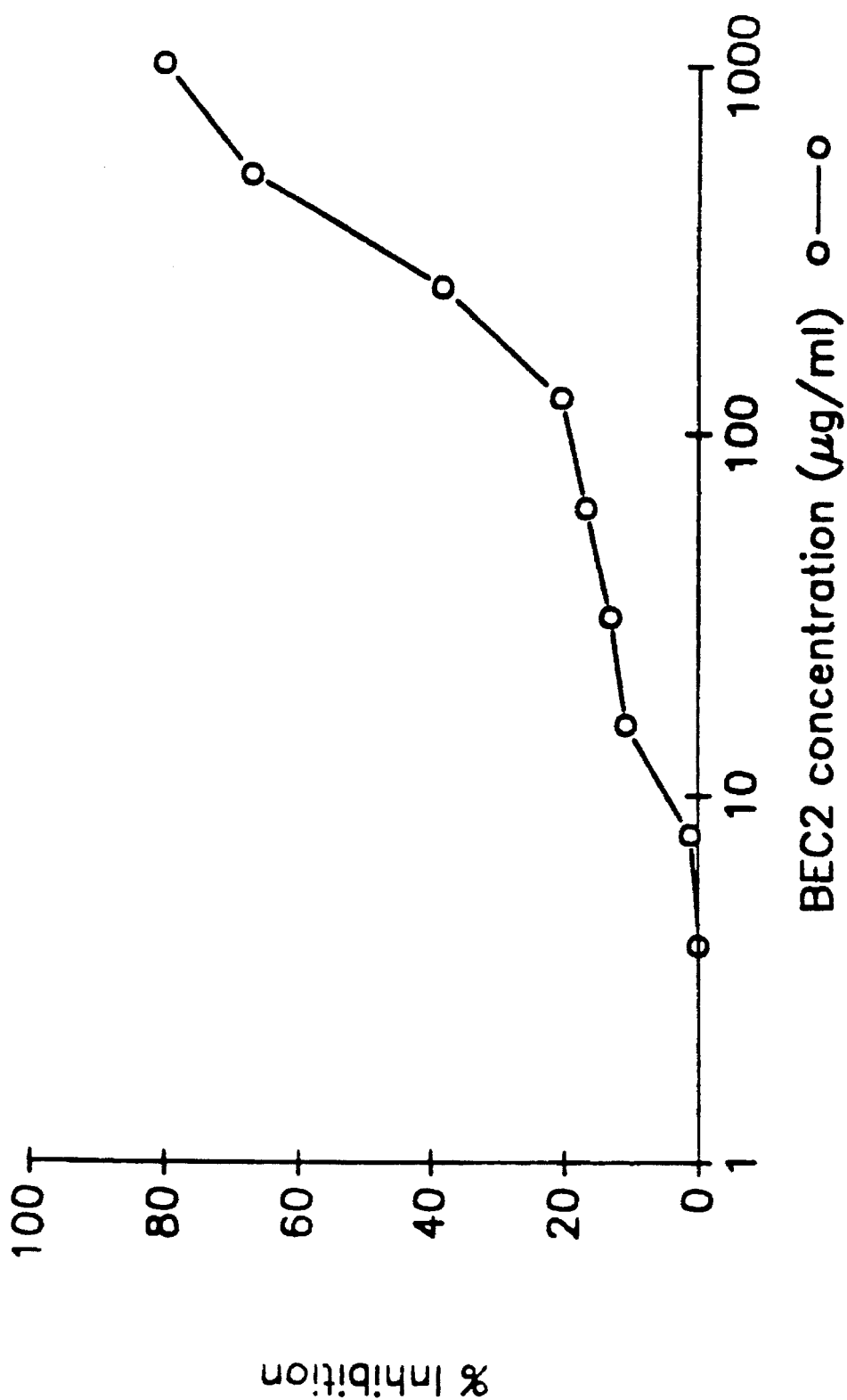
FIG. 4: Inhibition by BEC2 of R24 binding to GD3. Data shows significant inhibition of R24 binding to $GD_3$ by BEC2, this is consistent with BEC2 being an Ab 2β anti-idiotypic mAb.

An anti-idiotypic mAb which recognizes the paratope of the immunizing mAb is called an Ab2β anti-idiotypic mAb. One implication of this is that the paratope of BEC2 should mimic GD$_3$. If one imagines the R24 paratope as a template for GD$_3$, and both GD$_3$ and BEC2 fit that template, then BEC2 must resemble GD$_3$. Using serological assays, we show that BEC2 can inhibit the binding of R24 to GD$_3$. FIG. 4 shows the results on one experiment in which different concentrations of BEC2 were preincubated with a fixed dilution of biotinylated R24. The mixture was added to a well coated with GD$_3$ and the amount of R24 available for binding was measured by adding alkaline phosphatase-conjugated avidin. The data show significant inhibition of R24 binding to GD$_3$ by BEC2 which is consistent with BEC2 being an Ab2β anti-idiotypic mAb. In order to directly demonstrate that the paratope of BEC2 mimics GD$_3$, it is necessary to immunize animals with BEC2 and show that the animals develop antibodies to GD$_3$.

We immunized four New Zealand White Rabbits with BEC2 mixed with Freund's complete adjuvant. The animals received several booster immunizations mixed with Freund's incomplete adjuvant over approximately three months. The rabbits were bled periodically and the serum was assayed for anti-GD$_3$ reactivity using two different assays. The anti-GD$_3$ IgG response was measured by radio-immunoassay (RIA) using [$^{125}$I]-Protein A. The anti-GD$_3$ IgM response was measured by ELISA using alkaline phosphatase-conjugated goat anti-rabbit second antibody which was specific for the mu chain. The specificity of both the IgG and IgM response was analyzed by immunoblot assays against several gangliosides. In these assays, [$^{125}$I]-Protein A was used to visualize IgG binding while peroxidase-conjugated goat anti-rabbit (mu chain specific) antiserum was used to visualize IgM binding.

Figure 5:
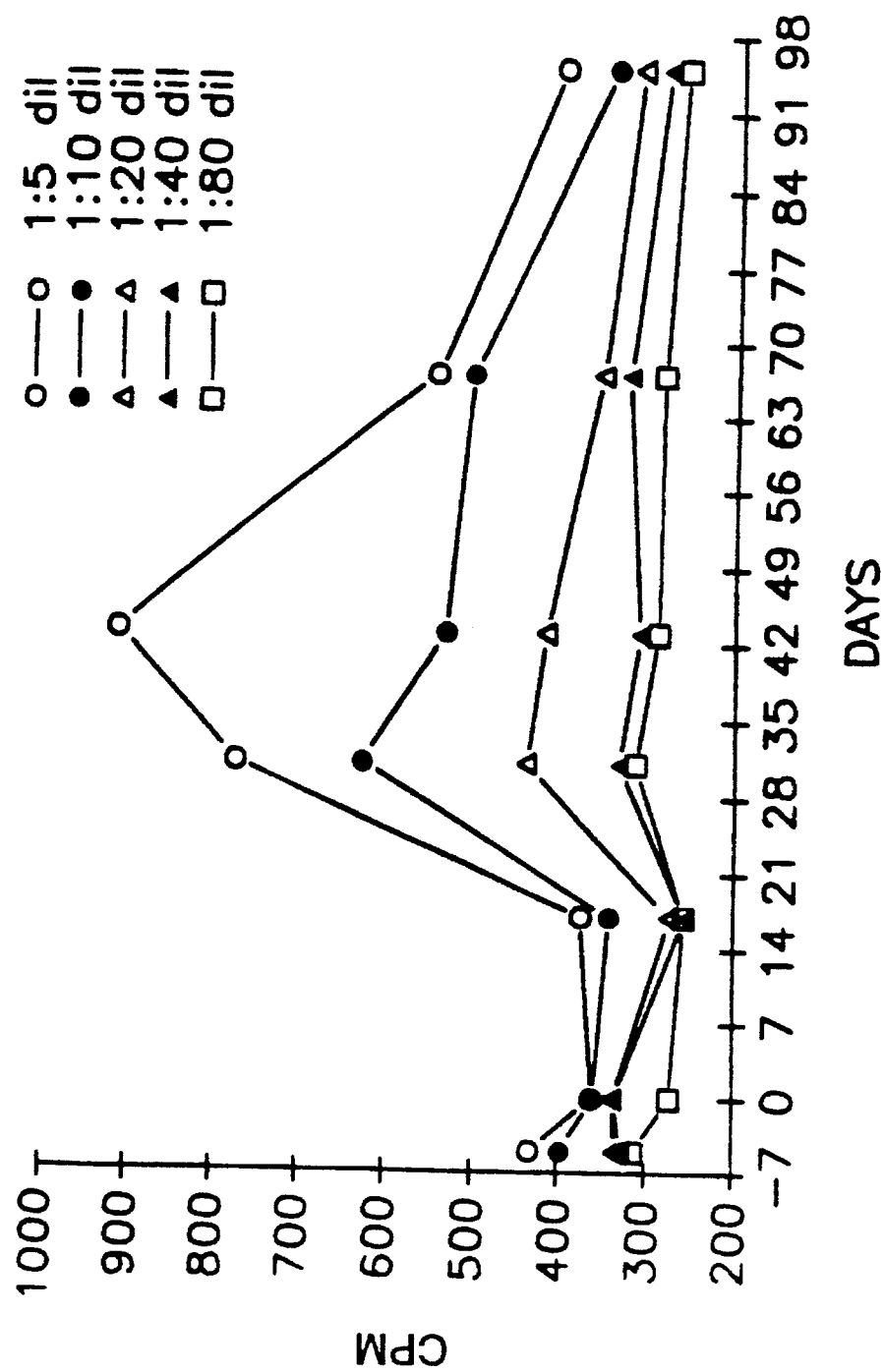
FIG. 5: Anti-$GD_3$ IgG of Rabbit 521 by RIA. Rabbit 521 developed IgG against $GD_3$ after being immunized with BEC2 mixed with Freund's complete adjuvant. The response was measured by RIA.
Figure 6:
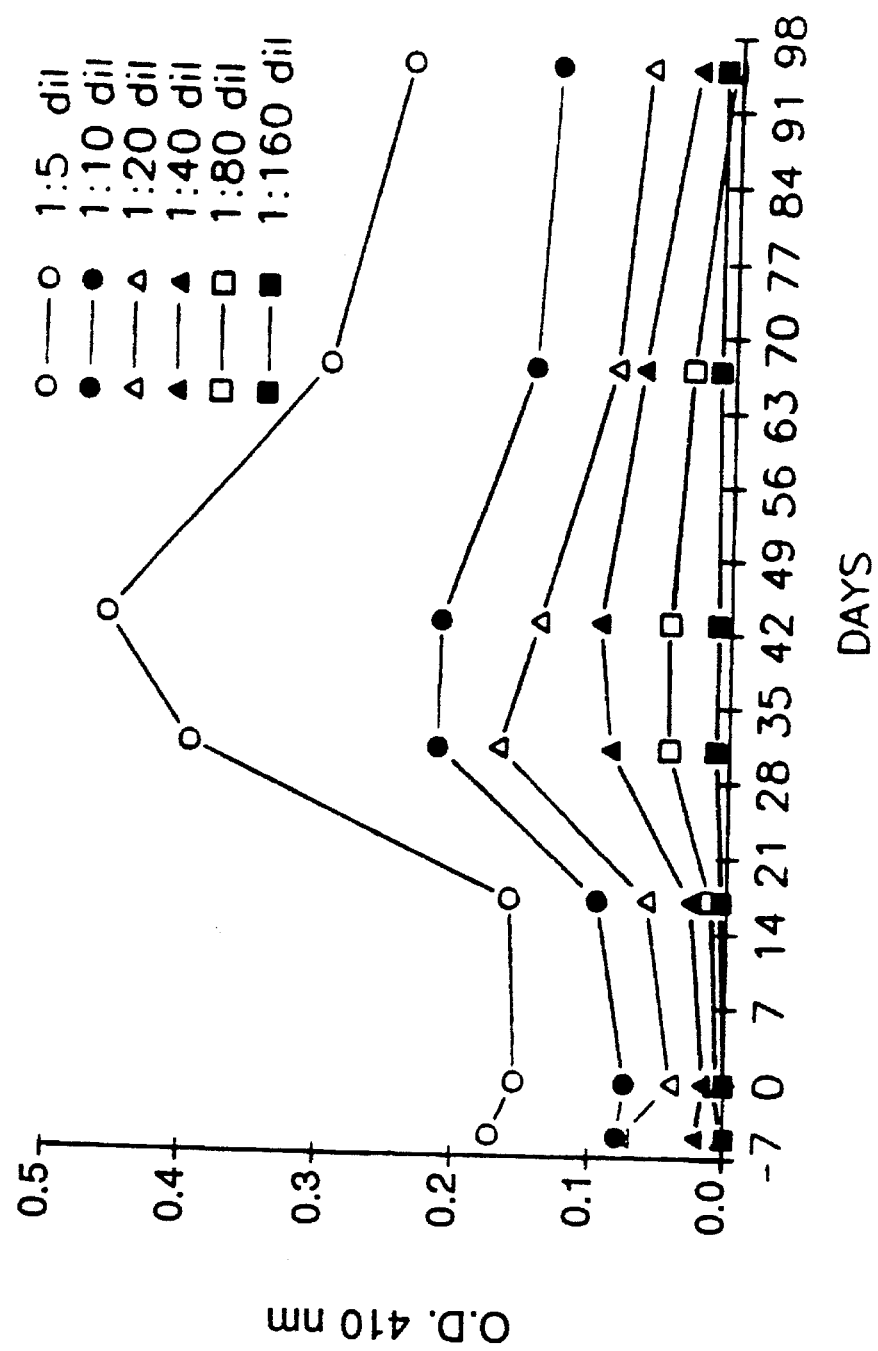
FIG. 6: Anti-$GD_3$ IgM of Rabbit 543 by ELISA. Rabbit 543 developed IgM after being immunized with BEC2 mixed with Freund's complete adjuvant. The response was measured by ELISA.
Figure 7:
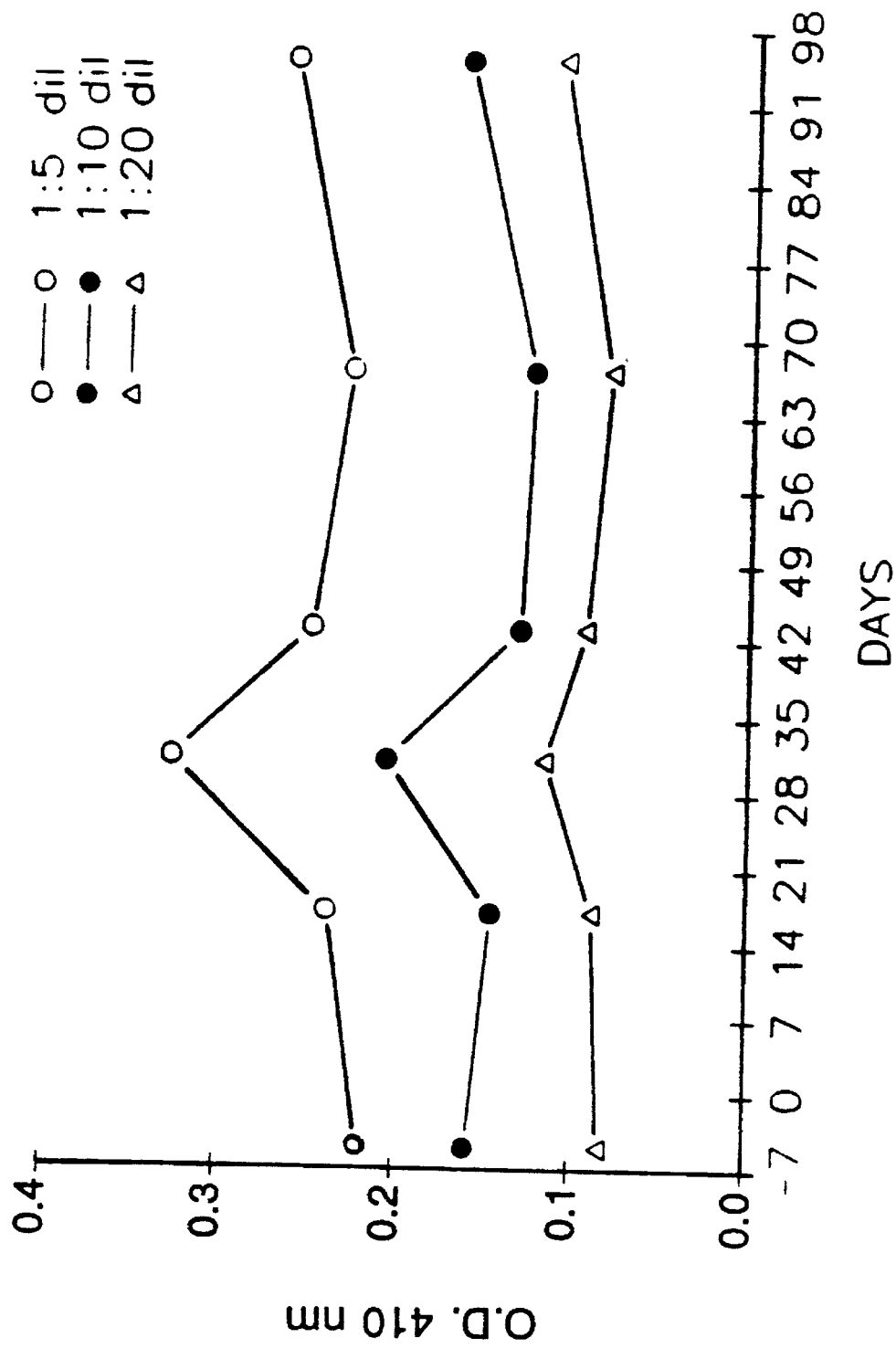
FIG. 7: Anti-$GD_3$ IgM of Rabbit 545 by ELISA. Rabbit 545 developed IgM after being immunized with BEC2 mixed with Freund's complete adjuvant. The response was measured by ELISA.
Figure 8:
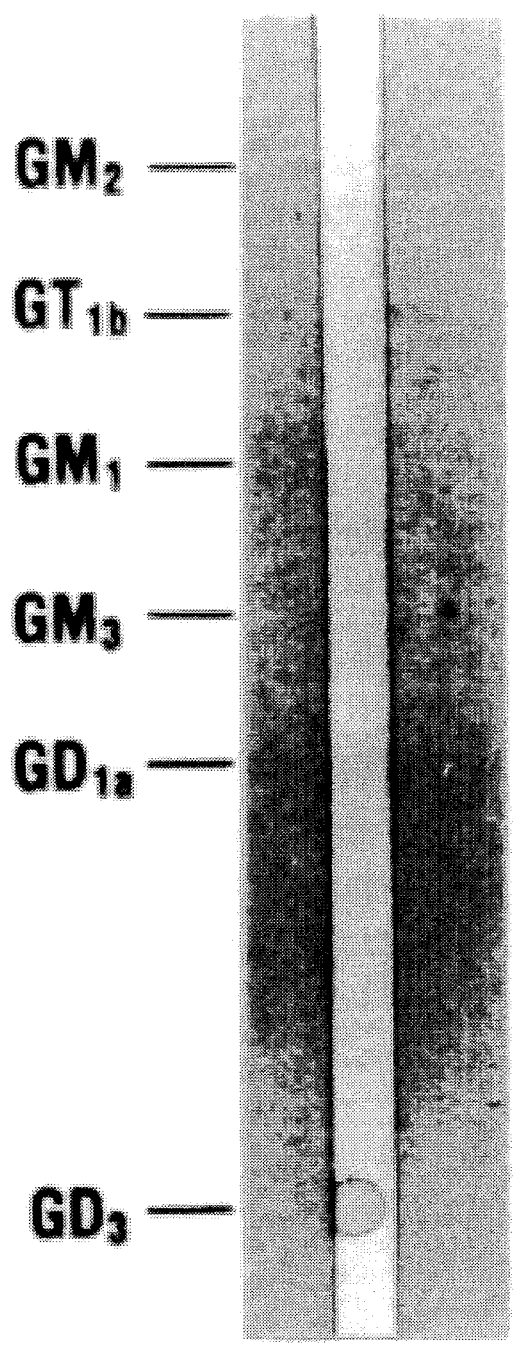
FIG. 8: Anti-$GD_3$ antibodies induced by BEC2 do not cross-react with other gangliosides. One μg of various purified gangliosides were applied to strips of nitrocellulose filters and allowed to dry. The strips were blocked in 5% non-fat milk and washed. Strips were incubated in rabbit serum (diluted 1:10) overnight. After washing, peroxidase-conjugated anti-rabbit IgM was added for 2 hours. The strips were again washed and binding was visualized by adding 4-chloro-1-napthol substrate with $H_2O_2$.

At least three of the four rabbits developed an anti-GD$_3$ antibody response. By RIA, Rabbit 521 developed IgG against GD$_3$ (FIG. 5) although by immunoblotting, all four rabbits appeared to make anti-GD$_3$ IgG. By ELISA, rabbits 543 (FIG. 6) and 545 (FIG. 7) developed IgM. The specificity of this antibody response was analyzed by immunoblot. FIG. 8 shows that IgM from rabbit 543 binds to GD$_3$ but not to the other five gangliosides tested (GM1, GM2, GM3, GD1a, GT1b). As noted above, immunoblotting of serum from all four rabbits showed evidence of IgG binding to GD$_3$ (data not shown) and this binding was specific.

Figure 9:
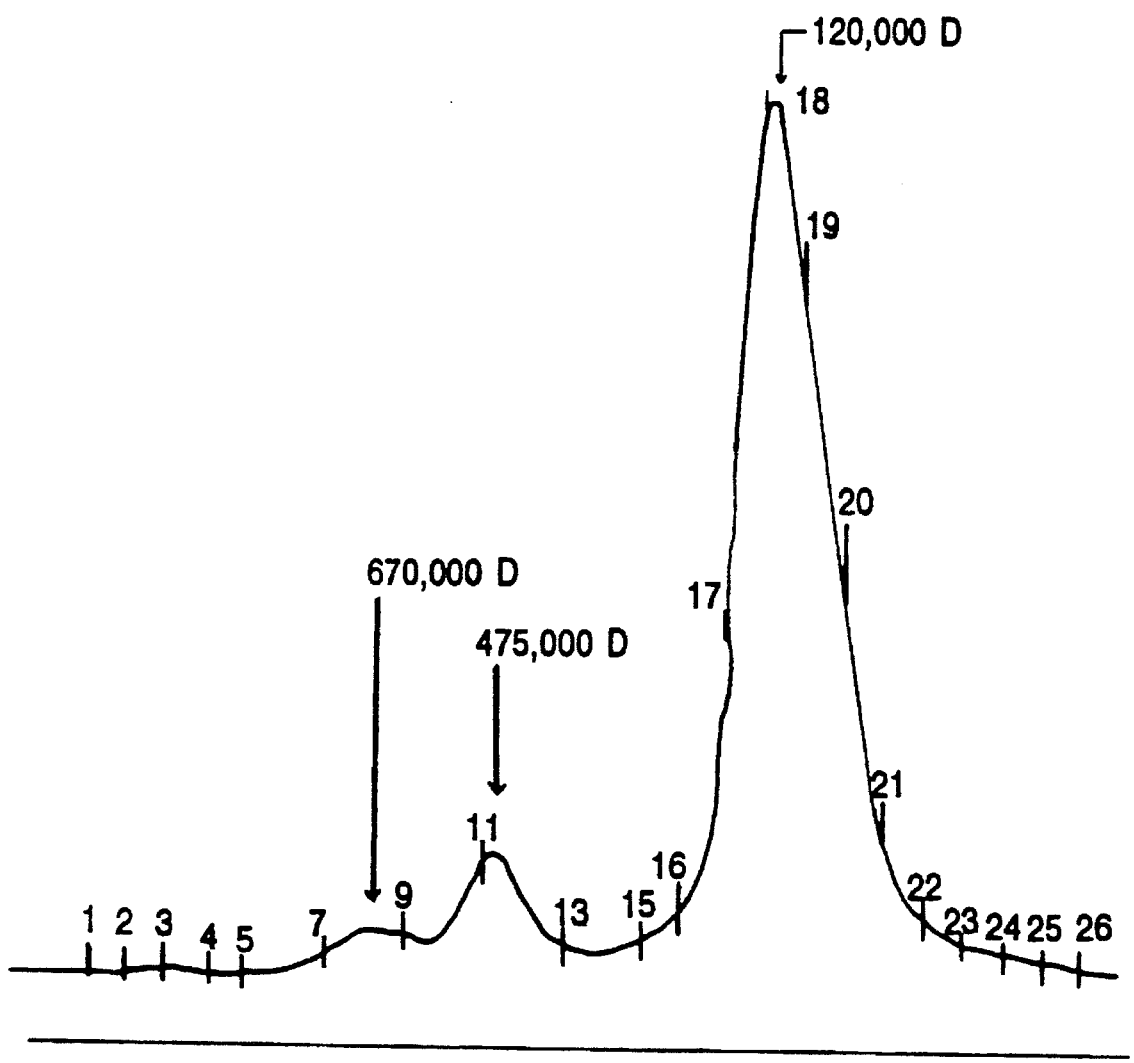
FIG. 9: Chromatogram showing that most proteins eluted at a molecular weight of approximately 120 kD which is consistent with IgG (145–150 kD) but not consistent with IgM (900 kD).
Figure 10:
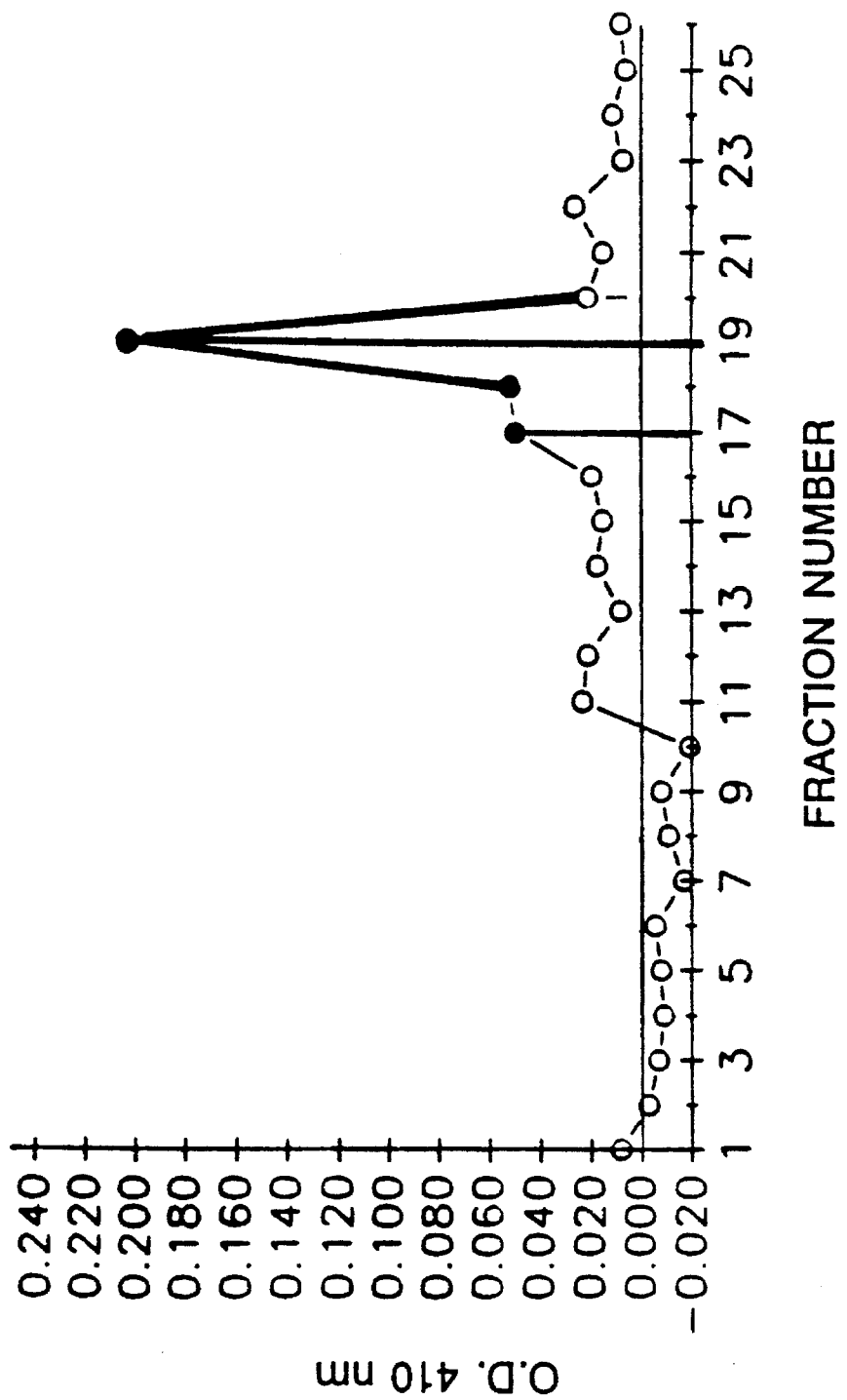
FIG. 10: Anti-$GD_3$ reactivity of $NH_4So_4$ precipitate from Rabbit 543. Graph showing the anti-$GD_3$ reactivity of each fraction. It is clear that only the 120 kD fraction is bound to $GD_3$.

In order to confirm that this anti-GD$_3$ reactivity was indeed IgG, serum from rabbit 543 was precipitated using 45% NH$_4$SO$_4$ and the immunoglobulin salted out was fractionated by size exclusion chromatography (Superose 6 column, Pharmacia). FIG. 9 shows that most of the protein eluted at a molecular weight of approximately 120 kD which is consistent with IgG (145–150 kD) but not consistent with IgM (900 kD). FIG. 10 shows the anti-GD$_3$ reactivity of each fraction and it is clear that only the 120 kD fraction bind to GD$_3$.

Results

BEC2 binds to the Fab region of R24 and blocks R24 binding to GD$_3$ gangliosides. Additionally, BEC2 binds to two other anti-GD$_3$ monoclonal antibodies, C5(IgG3) and K9 (IgM). Because BEC2 contains irrelevant light chains BEC2 neither binds to other mouse monoclonal antibodies, including four IgG3 monoclonal antibodies, nor binds to the variant of R24.

BEC2 is an AB2 anti-idiotypic monclonal antibody for it binds to the portion of R24 which recognizes GD$_3$. If one imagines the R24 binding site as a template for GD$_3$, and both GD$_3$ and BEC2 fit that template, then BEC2 must resemble GD$_3$. Using serological assays, we have shown that BEC2 does indeed resemble GD$_3$ from the immune system's point of view. BEC2 is a useful way to immunize against GD$_3$, and thus, important as a vaccine against melanoma and other tumors.

To demonstrate that BEC2 carries an internal image of GD$_3$, we immunized NZW rabbits with BEC2 and studied pre-immune and immune sera for evidence of anti-GD$_3$ reactivity. Immunized rabbits developed an antibody response to GD$_3$ detectable by ELISA and Immunoblot against purified GD$_3$, and by mixed hemadsorption assay against a GD$_3^+$ human melanoma cell line. Specificity analysis showed that immune sera recognized only GD$_3$ and not GM$_1$, GM$_2$, GM$_3$, GD$_{1a}$, or GT$_{1b}$, monoclonal antibody. BEC2 provides a strategy for active immunization of melanoma patients against GD3.

Immunization with BEC2 induces high titer, specific IgM and IgG antibodies to GD3 in rabbits and IgM antibodies in syngeneic (BALB/c×C57B1)F1 mice.

From the experiments, we find that BEC2 is a mouse IgG2b anti-idiotypic mAb directed against R24 and binds the antigen-binding site of R24. Further, immunization of rabbits with BEC2 results in an IgM and IgG response against GD$_3$. Finally, BEC2 carries the internal image of the ganglioside GD$_3$, therefore, it is useful for immunization against GD$_3$ gangliosides.

What is claimed is:

1. Monoclonal antibody BEC-2 produced by the hybridoma having ATCC Accession Number HB 10153.

2. A human-mouse chimeric antibody derived from the monoclonal antibody of claim 1.

3. The hybridoma designated BEC-2 hybridoma having ATCC Accession Number 10153.

4. The monoclonal antibody of claim 1 labelled with a detectable marker.

5. The monoclonal antibody of claim 4, wherein the detectable marker is an enzyme.

6. The monoclonal antibody of claim 4, wherein the detectable marker is a chromophore, a fluorophore, a radioisotope, or a heavy metal.

* * * * *